United States Patent
Kleiner

(10) Patent No.: US 9,833,344 B2
(45) Date of Patent: Dec. 5, 2017

(54) STENT MADE FROM AN ULTRA HIGH MOLECULAR WEIGHT BIOABSORBABLE POLYMER WITH HIGH FATIGUE AND FRACTURE RESISTANCE

(71) Applicant: ABBOTT CARDIOVASCULAR SYSTEMS INC., Santa Clara, CA (US)

(72) Inventor: Lothar W. Kleiner, Los Altos, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 15/280,845

(22) Filed: Sep. 29, 2016

(65) Prior Publication Data

US 2017/0014250 A1 Jan. 19, 2017

Related U.S. Application Data

(62) Division of application No. 12/422,783, filed on Apr. 13, 2009, now Pat. No. 9,492,587.

(51) Int. Cl.

| A61L 31/04 | (2006.01) |
|---|---|
| B05D 1/18 | (2006.01) |
| A61F 2/06 | (2013.01) |
| A61F 2/915 | (2013.01) |
| A61L 27/28 | (2006.01) |
| A61L 31/06 | (2006.01) |
| A61L 31/10 | (2006.01) |
| A61L 31/14 | (2006.01) |
| A61L 31/16 | (2006.01) |
| B05D 3/00 | (2006.01) |
| B05D 5/00 | (2006.01) |
| B05D 7/24 | (2006.01) |
| B05D 7/00 | (2006.01) |

(Continued)

(52) U.S. Cl.
CPC .............. *A61F 2/915* (2013.01); *A61L 27/28* (2013.01); *A61L 31/06* (2013.01); *A61L 31/10* (2013.01); *A61L 31/14* (2013.01); *A61L 31/148* (2013.01); *A61L 31/16* (2013.01); *B05D 1/18* (2013.01); *B05D 3/007* (2013.01); *B05D 5/00* (2013.01); *B05D 7/24* (2013.01); *B05D 7/544* (2013.01); *A61F 2/07* (2013.01); *A61F 2/30* (2013.01); *A61F 2002/30065* (2013.01); *A61F 2002/3067* (2013.01); *A61F 2002/91583* (2013.01); *A61L 2300/41* (2013.01); *A61L 2300/416* (2013.01); *A61L 2300/606* (2013.01)

(58) Field of Classification Search
CPC ....... A61L 31/041; A61L 31/148; B05D 1/18; A61F 2/06
USPC .......... 427/2.24, 2.25, 430.1; 623/1.38, 1.42
See application file for complete search history.

(56) References Cited

U.S. PATENT DOCUMENTS

2006/0018948 A1* 1/2006 Guire ...................... A61L 31/06
424/426
2007/0179219 A1* 8/2007 Huang ...................... A61F 2/82
524/37

(Continued)

*Primary Examiner* — Cachet Sellman
(74) *Attorney, Agent, or Firm* — Squire Patton Boggs (US) LLP

(57) ABSTRACT

A stent made from an ultra high molecular weight bioabsorbable polymer is disclosed herein. The bioabsorbable polymer can have a Mw greater than 1 million g/mole or greater than 2 million g/mole. Methods of making the ultra high molecular weight polymer stent without degrading the molecular weight are further disclosed.

2 Claims, 5 Drawing Sheets

(51) Int. Cl.
    *A61F 2/07*           (2013.01)
    *A61F 2/30*           (2006.01)

(56) References Cited

U.S. PATENT DOCUMENTS

| | | | | |
|---|---|---|---|---|
| 2007/0207186 A1* | 9/2007 | Scanlon | .................... | A61F 2/07 424/424 |
| 2009/0030505 A1* | 1/2009 | Kleiner | .................... | A61L 31/10 623/1.42 |
| 2009/0319028 A1* | 12/2009 | Ramzipoor | ............... | A61F 2/82 623/1.17 |
| 2010/0036478 A1* | 2/2010 | Wang | ..................... | A61L 31/06 623/1.15 |

\* cited by examiner

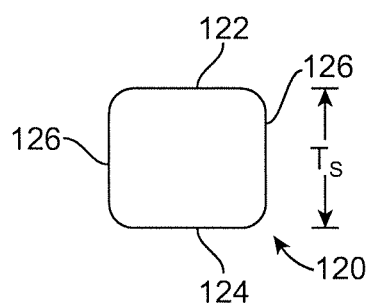
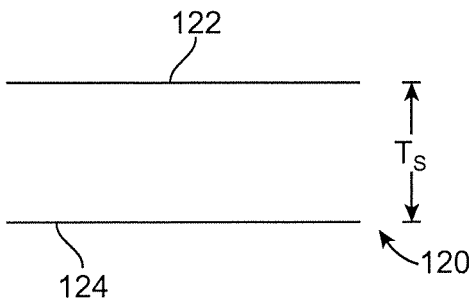
FIG. 2A          FIG. 2B
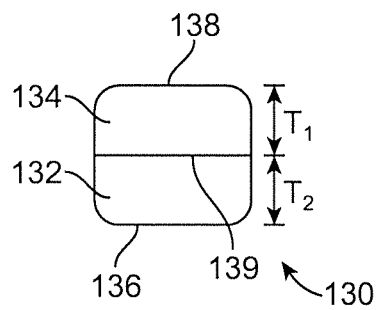
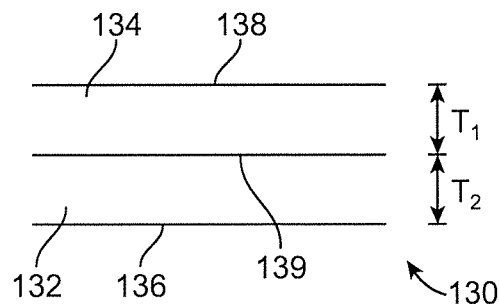
FIG. 3A          FIG. 3B
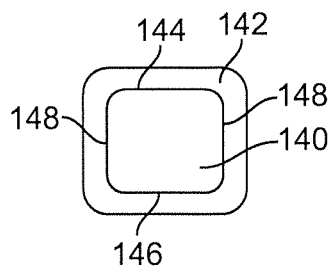
FIG. 4

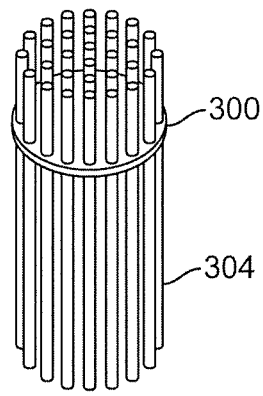
FIG. 7
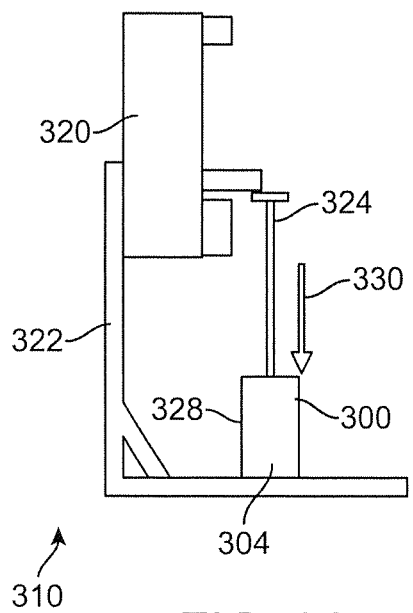 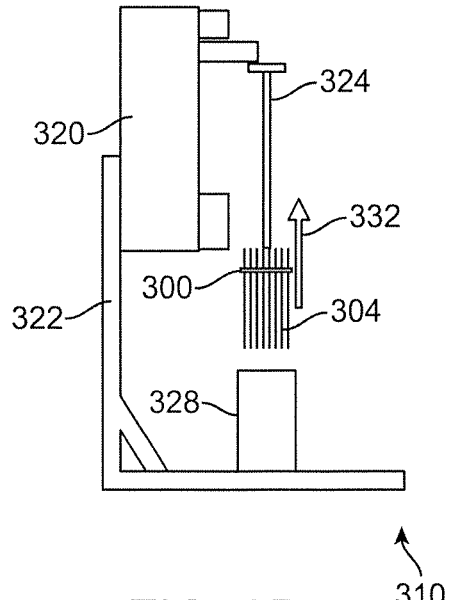
FIG. 8A  FIG. 8B

STENT MADE FROM AN ULTRA HIGH MOLECULAR WEIGHT BIOABSORBABLE POLYMER WITH HIGH FATIGUE AND FRACTURE RESISTANCE

This application is a divisional application of U.S. patent application Ser. No. 12/422,783 filed Apr. 13, 2009, which is incorporated by reference herein.

BACKGROUND OF THE INVENTION

Field of the Invention

This invention relates to methods of manufacturing polymeric medical devices, in particular, stents.

Description of the State of the Art

This invention relates to radially expandable endoprostheses, that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices that function to hold open and sometimes expand a segment of a blood vessel or other anatomical lumen such as urinary tracts and bile ducts.

Stents are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success. Stent are also used widely in endovascular applications, such as in the popliteal artery.

Stents are typically composed of scaffolding that includes a pattern or network of interconnecting structural elements or struts, formed from wires, tubes, or sheets of material rolled into a cylindrical shape. This scaffolding gets its name because it physically holds open and, if desired, expands the wall of the passageway. Typically, stents are capable of being compressed or crimped onto a catheter so that they can be delivered to and deployed at a treatment site.

Delivery includes inserting the stent through small lumens using a catheter and transporting it to the treatment site. Deployment includes expanding the stent to a larger diameter once it is at the desired location. Mechanical intervention with stents has reduced the rate of restenosis as compared to balloon angioplasty. Yet, restenosis remains a significant problem. When restenosis does occur in the stented segment, its treatment can be challenging, as clinical options are more limited than for those lesions that were treated solely with a balloon.

Stents are used not only for mechanical intervention but also as vehicles for providing biological therapy. Biological therapy uses medicated stents to locally administer a therapeutic substance. Effective concentrations at the treated site require systemic drug administration which often produces adverse or even toxic side effects. Local delivery is a preferred treatment method because it administers smaller total medication levels than systemic methods, but concentrates the drug at a specific site. Local delivery thus produces fewer side effects and achieves better results.

A medicated stent may be fabricated by coating the surface of either a metallic or polymeric scaffolding with a polymeric carrier that includes an active or bioactive agent or drug. Polymeric scaffolding may also serve as a carrier of an active agent or drug.

The stent must be able to satisfy a number of mechanical requirements. The stent must be capable of withstanding the structural loads, namely radial compressive forces, imposed on the stent as it supports the walls of a vessel. Therefore, a stent must possess adequate radial strength. Radial strength describes the external pressure that a stent is able to withstand without incurring clinically significant damage. Additionally, a stent should be sufficiently rigid to adequately maintain its size and shape throughout its service life despite the various forces that may come to bear on it, including the cyclic loading induced by the beating heart. For example, a radially directed force may tend to cause a stent to recoil inward. Furthermore, the stent should possess sufficient toughness or resistance to fracture from stress arising from crimping, expansion, and cyclic loading.

Some treatments with implantable medical devices require the presence of the device only for a limited period of time. Once treatment is complete, which may include structural tissue support and/or drug delivery, it may be desirable for the stent to be removed or disappear from the treatment location. One way of having a device disappear may be by fabricating the device in whole or in part from materials that erode or disintegrate through exposure to conditions within the body. Thus, erodible portions of the device can disappear or substantially disappear from the implant region after the treatment regimen is completed. After the process of disintegration has been completed, no portion of the device, or an erodible portion of the device will remain. In some embodiments, very negligible traces or residue may be left behind. Stents fabricated from biodegradable, bioabsorbable, and/or bioerodable materials such as bioabsorbable polymers can be designed to completely erode only after the clinical need for them has ended. However, there are potential shortcomings in the use of polymers as a material for stents such as low fracture toughness.

SUMMARY OF THE INVENTION

Various embodiments of the present invention include a stent comprising a stent body for supporting a vascular lumen, wherein the stent body is formed of a bioabsorbable polymer, wherein the bioabsorbable polymer has a weight average molecular weight greater than 1 million g/mole.

Additional embodiments of the present invention include a method of making a stent body for supporting a vascular lumen, comprising: immersing a cylindrical member in a solution including a bioabsorbable polymer dissolved in a fluid, wherein the bioabsorbable polymer has an inherent viscosity greater than 6 dl/g in chloroform at 25° C. or has a weight average molecular weight greater than 1 million g/mole, removing the member from the solution, wherein a portion of the solution remains on the surface of the member upon removal from the solution; removing solvent from the solution remaining on the member to form a tubular layer of the bioabsorbable polymer on the member; repeating the immersion step, removal from the solution step, and removal of the solvent step to form a final tubular layer of bioabsorbable polymer on the member of a desired thickness; and forming a stent body from the final tubular layer.

BRIEF DESCRIPTION OF THE DRAWINGS

FIGS. 2A-B depict a cross-section of a strut of a stent body transverse to its longitudinal axis and along its longitudinal axis, respectively.

FIGS. 3A-B depict a cross-section of a strut of a stent body or scaffolding transverse to its longitudinal axis and along its longitudinal axis, respectively.

FIG. 4 depicts a transverse cross-section of a strut with a coating layer.

FIG. 7 depicts a mandrel mounting disk having a plurality of holes configured to hold mandrels for a dip coating operation.

FIG. 8A depicts a system for controlled dip coating of mandrels mounted on the mounting disk of FIG. 7.

FIG. 8B shows the system of FIG. 8A with the mounting disk and mounted mandrels removed from a solution.

DETAILED DESCRIPTION OF THE INVENTION

Various embodiments of the present invention relate to implantable medical devices, such as stents made from bioabsorbable polymers that provide high fatigue and fracture resistance. These bioabsorbable polymers have an ultra high molecular weight, which provide the high fatigue and fracture resistance as compared to typical bioabsorbable polymers with much lower molecular weights fabricated by typical melt processing techniques such as extrusion or injection molding. The embodiments further include methods of fabricating the stent. The embodiments are generally applicable to any tubular polymeric implantable medical device. In particular, the methods can be applied to tubular implantable medical devices such as self-expandable stents, balloon-expandable stents, and stent-grafts.

Figure 1:
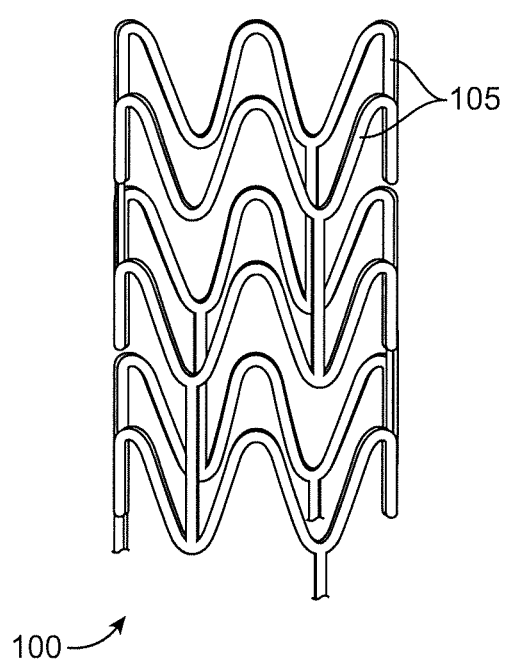
FIG. 1 depicts a stent.

A stent may include a pattern or network of interconnecting structural elements or struts. FIG. 1 depicts a view of a stent 100. In some embodiments, a stent may include a body, backbone, or scaffolding having a pattern or network of interconnecting struts or structural elements 105. Stent 100 may be formed from a tube (not shown). The structural pattern of the device can be of virtually any design. The embodiments disclosed herein are not limited to stents or to the stent pattern illustrated in FIG. 1. The embodiments are easily applicable to other patterns and other devices. The variations in the structure of patterns are virtually unlimited. A stent such as stent 100 may be fabricated from a tube by forming a pattern with a technique such as laser cutting or chemical etching.

A stent such as stent 100 may be fabricated from a polymeric tube or a sheet by rolling and bonding the sheet to form the tube. A tube or sheet for making a stent are conventionally formed by extrusion or injection molding. A stent pattern, such as the one pictured in FIG. 1, can be formed in a tube or sheet with a technique such as laser cutting or chemical etching. The stent can then be crimped on to a balloon or catheter for delivery into a bodily lumen.

An implantable medical device can be made partially or completely from a biodegradable, bioabsorbable, or biostable polymer. A polymer for use in fabricating an implantable medical device can be biostable, bioabsorbable, biodegradable or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and absorption of the polymer can be caused by, for example, hydrolysis and metabolic processes.

A stent made from a biodegradable polymer is intended to remain in the body for a duration of time until its intended function of, for example, maintaining vascular patency and/or drug delivery is accomplished. After the process of degradation, erosion, absorption, and/or resorption has been completed, no portion of the biodegradable stent, or a biodegradable portion of the stent will remain. In some embodiments, very negligible traces or residue may be left behind.

The duration of a treatment period depends on the bodily disorder that is being treated. In treatments of coronary heart disease involving use of stents in diseased vessels, the duration can be in a range from about a month to a few years. However, the duration is typically up to about six months, twelve months, eighteen months, or two years. In some situations, the treatment period can extend beyond two years. The stent is expected to be completely degraded away from the vessel at the end of the treatment period.

As indicated above, a stent has certain mechanical requirements such as high radial strength, high modulus, high fracture toughness, and high fatigue resistance including bending fatigue for endovascular applications. A stent that meets such requirements greatly facilitates the delivery, deployment, and treatment of a diseased vessel. A polymeric stent with inadequate mechanical properties can result in mechanical failure, strut fracture, or recoil inward after implantation into a vessel.

With respect to radial strength, the strength to weight ratio of polymers is usually smaller than that of metals. To compensate for this, a polymeric stent can require significantly thicker struts than a metallic stent, which results in an undesirably large profile.

Additionally, polymers that are sufficiently rigid to support a lumen at conditions within the human body may also have low fracture toughness since they may exhibit a brittle fracture mechanism. For example, these include polymers that have a glass transition temperature (Tg) above human body temperature (Tbody), which is approximately 37° C. Such polymers may exhibit little or no plastic deformation prior to failure. It is important for a stent to be resistant to fracture throughout the range of use of a stent, i.e., crimping, delivery, deployment, and during a desired treatment period. In particular, stents used in endovascular applications, such as in the popliteal, are highly susceptible to fracture as a result of severe bending and torsional fatigue that occurs in the peripheral anatomy as a result of walking, running, sitting and other physical activity. PLLA is but one example of the class of semicrystalline polymers for which the above description is true. The Tg of PLLA varies between approximately 50 to 80° C., or more narrowly between 55 and 65° C., depending on crystallinity, microstructure, and molecular weight.

A tubular polymer perform or construct, such as a tube, sheet, or fibers, from can be made from a polymer melt of semicrystalline polymers from methods such as extrusion or injection molding. The constructs produced from these methods and the devices, such as a stent, made therefrom are fairly brittle and have a low elongation to fracture. Such stents can be prone to fracture when they are crimped and deployed. Additionally, such stents may have insufficient strength to adequately support a lumen.

The weight average molecular weight (Mw) of polymers that is typically used for forming constructs for fabricating medical devices is in the range of about 100,000 to 600,000 g/mole or have an inherent viscosity of less than about 4 dl/g. In this range, the viscosity of melts of such polymers is low enough to allow melt processing at temperatures that do not significantly degrade the molecular weight of the polymer (between 20 to 30%). Without further processing or material modification, of such constructs, the mechanical properties are limited by the low molecular weight. Additionally, further processing steps, in particular radiation sterilization, can further degrade the molecular weight. For example, for a starting (e.g., an extruded tube) molecular weight, Mw, of 600,000 g/mole, the molecular weight can decrease to Mw of 190,000 g/mole after e-beam sterilization with a dose of 20-30 kGy.

Various embodiments of the present invention include a stent having a stent body or scaffolding formed, fabricated from, or consisting essentially of a bioabsorbable polymer having an ultra high molecular weight (UHMW). The UHMW corresponds to a Mw that is greater than 1 million g/mole and an Mn greater than 500,000 g/mole. The polymer constructs and stent made therefrom may be formed from polymers with a Mw between 1-1.2 million g/mole, 1.2-1.5 million g/mole, 1.5 to 1.7 million g/mole, 1.7-2 million g/mole, 2 million g/mole, or greater than 2 million g/mole. Alternatively or additionally, the bioabsorbable polymer has an inherent viscosity of greater than 8 dl/g in chloroform at 25° C. Polymer constructs with such a molecular weight range may be obtained from solvent processing methods adapted to solutions of ultra high molecular weight polymers. The UHMW polymer constructs and stents formed therefrom have high strength, high stiffness (modulus), high fracture toughness, and good fatigue resistance.

A polymer construct composed of a UHMW as indicated above cannot be fabricated using melt processing methods such as extrusion or injection molding. Therefore, a stent body composed of a UHMW polymer made by machining a stent pattern from a tube cannot be fabricated through melt processing. The inventors have found that at the temperatures of melt processing of polymers with a conventional range of Mw or inherent viscosity, the viscosity of the UHMW polymer melts is too high to process. Alternatively, the inventors have also found that melt processing the UHMW polymer at higher temperatures to reduce the viscosity of the melt results in significant molecular weight degradation of the polymer, so that the polymer in the construct that is formed does not have a UHMW.

In some embodiments, the UHMW polymer of the construct and stents made therefrom is a semicrystalline polymer. In such embodiments, the polymer may have a Tg above Tbody. In order to provide greater stability of the stent at conditions within a human body, the Tg may be at least 10, 20, or 30° C. greater than human body temperature, which is about 37° C. The Tg of this polymer as measured by DSC is approximately 64° C. at a scan rate of 20° C. per minute as measured by taking the half-height in the ΔCp region of (change in heat capacity) of the DCS thermogram.

An exemplary UHMW polymer can be UHMW PLLA. The degree of crystallinity of a UHMW PLLA construct can be 10-40%, or more narrowly, 15-25%, however, the degree of crystallinity can be lower than 15% or greater than 25% and depends on processing conditions. The degree of crystallinity is as measured by DSC and assuming $\Delta H_f^o$ is 93.7 joules/gram 100% crystallinity. The Tg of the UHMW PLLA may be between about 63-65° C. and the Tm of the UHMW PLLA may be between 174-178° C. as measured by DSC at a scan rate of 20° C. per minute. If the PLLA is blended with PDLA to form a stereocomplex, then the Tm can be as high as 230. A significant advantage of the UHMW polymer is that it is expected to provide very high fracture toughness and elongation without sacrificing modulus and radial strength for a stent with a relatively low degree of crystallinity (e.g., less than 25%, or more narrowly less than 15%, with a lower degree of crystallinity preferred), which minimizes brittle behavior. The inventor has found that polymers in the conventional or typical molecular weight range should have a degree of crystallinity of greater than about 40-50% to provide sufficient radial strength and modulus for a stent to support a blood vessel (e.g., support for at least 1-3 months with less than 10% recoil). Such high degree of crystallinity provides a greater risk of brittle behavior during use of a stent.

The body, scaffolding, or substrate of a stent may be primarily responsible for providing mechanical support to walls of a bodily lumen once the stent is deployed therein. A stent body, scaffolding, or substrate, for example, as pictured in FIG. 1, can refer to a stent structure with an outer surface to which no coating or layer of material different from that of which the structure is manufactured. If the body is manufactured by a coating process, the stent body can refer to a state prior to application of additional coating layers of different material. "Outer surface" refers to any surface however spatially oriented that is in contact with bodily tissue or fluids. A stent body, scaffolding, or substrate can refer to a stent structure formed by laser cutting a pattern into a tube or a sheet that has been rolled into a cylindrical shape.

In some embodiments, the stent body, scaffolding, struts, or structural elements of the present invention may be nonporous or substantially nonporous. Substantially nonporous refers to a porosity of less than 0.1 percent. Alternatively, the stent body, scaffolding, struts, or structural elements of the present invention may be porous. Additionally, the surface of the stent body, scaffolding, struts, or structural elements of the present invention may have cavities or alternatively, be cavity-free.

Exemplary semicrystalline polymers that may be used in embodiments of the present invention include poly(L-lactide) (PLLA), polyglycolide (PGA), polymandelide (PM), polycaprolactone (PCL), poly(trimethylene carbonate) (PTMC), polydioxanone (PDO), poly(4-hydroxy butyrate) (PHB), and poly(butylene succinate) (PBS). An exemplary amorphous polymer that may be used includes poly(DL-lactide) (PDLLA). Additionally, block, random, and alternating copolymers of the above polymers may also be used in embodiments of the present invention, for example, poly(L-lactide-co-glycolide). PLLA, PM, PGA, PDLLA, and PLGA have Tg's above human body temperature.

FIGS. 2A-B depict cross-sections of a strut 120 of a stent body transverse to its longitudinal axis and along its longitudinal axis, respectively. Strut 120 has an abluminal surface 122, a luminal surface 124, and sidewall surfaces 126. Strut 120 has a thickness Ts, which corresponds to the thickness of a tubular construct from which the stent body is machined. An exemplary range of Ts for a polymer stent scaffolding to adequately support a vessel is between 0.004-0.008 in.

In further embodiments, the struts or structural elements of a stent can have two or more layers transverse to the radial direction of the stent. Radial direction corresponds direction defined by the shortest line from a point on the structural element to the cylindrical axis of the stent. Each of the layers on the sidewalls of the structural element may be free of a material different from a respective layer. In such embodiments, the adjacent layers are composed of materials with different properties or characteristics. Different properties or characteristics can refer to different chemical composition of a polymers, differing composition due to blending of polymers, differing composition due to blending of filler materials, molecular weight, or a combination thereof.

The two or more layers can include an abluminal layer, a luminal layer, and one or more layers between the abluminal and luminal layers. FIGS. 3A-B depict cross-sections of a strut 130 of a stent body or scaffolding transverse to its longitudinal axis and along its longitudinal axis, respectively. Strut 130 has a luminal layer 132 and an abluminal layer 134. A surface 139 is a boundary between the two layers. Luminal layer 132 has a luminal surface 136 and abluminal layer 134 has an abluminal surface 138. Abluminal layer 134 has a thickness T1 and luminal layer 132 has thickness T2.

In some embodiments, one of the layers is an UHMW polymer and other layers can be made of a low molecular weight polymer with a Mw that is in a conventional range, for example, less than 300,000 g/mole. In an exemplary embodiment, the luminal layer can be made of an UHMW polymer and the abluminal layer can be a low molecular weight layer, although the layers could be reversed. The ratio of the thicknesses of the UHMW layer and the low molecular weight layer can vary, for example, between 1000:1 to 2:1. In other embodiments, adjacent layers can be made from UHMW polymers, but the polymers in the different layers have different Mw.

The use of low molecular weight layer(s) with a UHMW layer allows adjustment of the degradation time (i.e., time for stent to completely erode from an implant site) to a desired range. A UHMW polymer layer has a longer degradation time than a lower molecular weight polymer layer. A strut will lose structural integrity and disintegrate faster as the thickness of the UHMW is decreased. Additionally, the low molecular weight layer can be a therapeutic layer. The low molecular weight polymer can have a therapeutic substance dispersed therein. For example, the ratio an UHMW layer to a low molecular weight layer can be 500:1 to 1000:1 with the low molecular weight layer being a therapeutic layer.

In further embodiments, the struts or structural elements of the scaffolding or body of the stent made from a UHMW polymer can have a polymer coating layer disposed partly or completely around the surface of the strut or structural element. FIG. 4 depicts a transverse cross-section of a strut 140 with a coating layer 142 disposed above an abluminal surface 144, luminal surface 146, and sidewall surfaces 148 of strut 140. Alternatively, the coating can be disposed exclusively above the abluminal layer, luminal layer, or both the luminal and abluminal layers. In such embodiments, the coating includes a polymer and therapeutic agent. The coating may have s Mw, for example between 50,000 to 300,000 g/mole. An exemplary embodiment is a UHMW PLLA scaffolding with a PDLA coating.

In further embodiments, a UHMW polymer scaffolding can have a therapeutic agent dispersed within and throughout the scaffolding polymer. The agent may be released into a vessel through diffusion from the scaffolding. Alternatively or additionally, the agent may be released due to erosion of the scaffolding. The agent, for example, can be an anti-inflammatory substance that reduces or eliminates inflammation to the vessel caused by degradation by-products of the scaffolding polymer. The scaffolding can alternatively or additionally include an antiproliferative agent. Exemplary antiproliferative and anti-inflammatory agents include everolimus and clobetasol, respectively.

Solvent processing generally refers to forming a polymer construct such as a tube from solution of polymer dissolved in a solvent. In embodiments of the present invention, solvent processing methods can be applied and adapted to making a bioabsorbable polymer construct in which the polymer is an UHMW polymer. Examples of solvent processing methods include spray coating, gel extrusion, supercritical fluid extrusion, roll coating and dip coating.

Due to the high viscosity of the UHMW polymer, traditional melt extrusion is not possible because the temperatures and pressures required cause excessive degradation of the polymer. However, some melt processing is may still possible without excessive degradation including ram extrusion and compression molding. However, the solvent processing techniques described below are preferred for making stents.

The embodiments include applying gel extrusion to fabricate a construct made from a UHMW polymer. In these embodiments, a polymer solution containing a UHMW polymer dissolved in a solvent is conveyed through an extruder. Gel extrusion is described in patent application Ser. No. 11/345,073 and is incorporated by reference herein in its entirety. The embodiments described therein can be applied to the UHMW polymers. In gel extrusion, the polymer solution has a viscosity low enough to be extruded at temperatures below the melting point of the polymer. These relatively low temperatures cause no or substantially no molecular weight degradation during the extrusion process. The solution is conveyed through a die at an end of the extruder to form a polymer construct such as tube. The solvent is removed from the polymer as it exits the die by quenching the exiting polymer, for example, in a water bath.

Spray coating typically involves mounting or disposing construct such as a tube onto a support, followed by spraying a coating material (such as a polymer solution) from a nozzle onto the mounted stent. A spray apparatus, such as EFD 780S spray device with VALVEMATE 7040 control system (manufactured by EFD Inc., East Providence, R.I., can be used to apply a coating material to the construct. An EFD 780S spray device is an air-assisted external mixing atomizer. The coating material is atomized into small droplets by air and uniformly applied to the construct surface. Other types of spray applicators, including air-assisted internal mixing atomizers and ultrasonic applicators, can also be used for the application of the coating material. To facilitate uniform and complete coverage of the construct during the application of the composition, a tube can be rotated about the tube's central longitudinal axis. The tube can also be moved in a linear direction along the same axis.

After application of the solution by spraying, the solvent is removed from the applied solution which leaves a layer of polymer on the surface of the construct. Drying or solvent removal depends on the volatility of the particular solvent employed, the solvent can evaporate essentially upon contact with the stent. Alternatively, the solvent can be removed by subjecting the coated stent to various drying processes, described below.

In embodiments of the present invention, a tubular coating layer can be formed over a mandrel by spray coating with a solution of an UHMW polymer. The tubular coating layer can then be removed from the mandrel and a stent can be formed from the tubular coating layer. A tubular coating layer of a desired thickness can be obtained by multiple repetitions of spraying and drying.

Dip coating is a method of forming a coating layer onto an object which includes immersing the object in a coating material or solution that includes a polymer dissolved in a solvent, withdrawing the object from the solution, and removing solvent from the solution retained on the surface of the object. Upon removal of the solvent, a layer of polymer is formed on the surface of the object. The steps above can be repeated to form multiple layers of polymer over the object to obtain a desired thickness of a coating layer.

In embodiments of the present invention, a polymer layer is formed over an object by immersing the object in a solution including an UHMW polymer in a solvent. The object is withdrawn and solvent is removed from the UHMW polymer solution retained on the object to form a UHMW coating layer on the object. The steps can be repeated to form a coating layer over the object of a desired thickness.

The object can be a cylindrical member or mandrel over which a tubular coating layer is formed. For both spray coating and dip coating, the mandrel can be made of any material that is not soluble in the solvent of the polymer solution. In some embodiments, the mandrel is made of a metal such as aluminum or stainless steel. In other embodiments, the mandrel is made from a glass with a polished surface. In some other embodiments, the mandrel is made of a soluble material that is insoluble in the solvent used for the coating. The coating layer is formed so that its radial thickness or the thickness of the wall of the tubular layer is the desired thickness of a stent scaffolding. The coating layer may then be removed from the mandrel and machined to form a stent scaffolding.

Figures 5A, 5B, 5C:
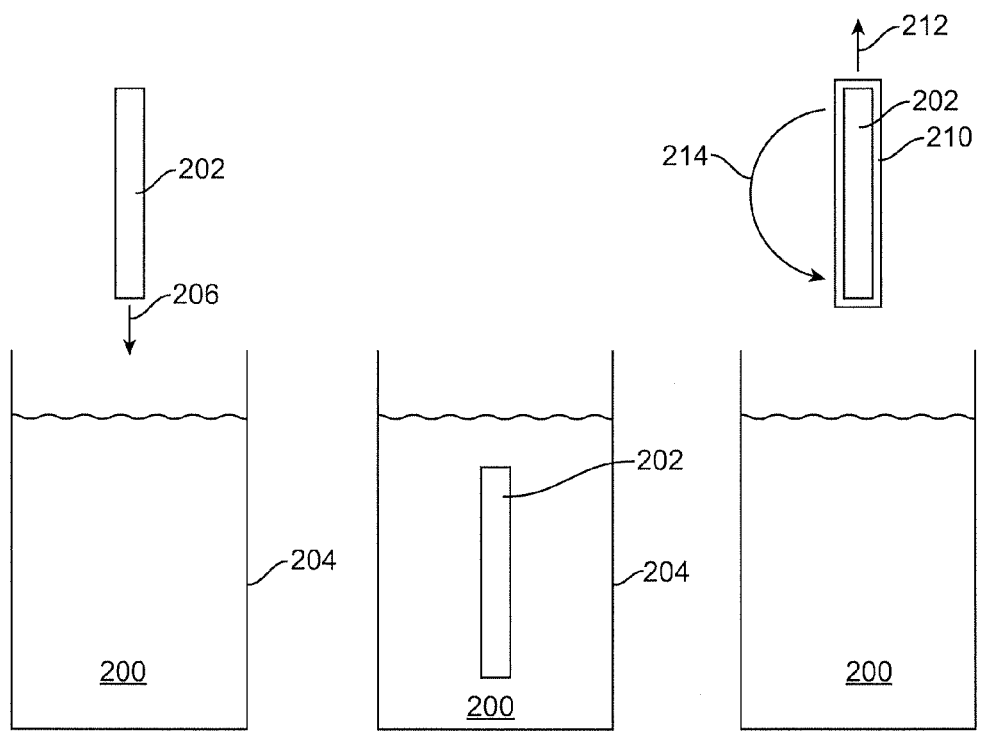
FIGS. 5A-C illustrate the dip coating process of the present invention.

FIGS. 5A-C illustrate the dip coating process of the present invention. As shown in FIG. 5A, a mandrel 202 is lowered, as shown by an arrow 206 into a container 204 having a solution 200 that includes a UHMW polymer dissolved in a solvent. The cylindrical axis of the mandrel is perpendicular to the surface of the solution, although the mandrel can be immersed at an angle different from 90° to the solution surface. As shown in FIG. 5B, the mandrel remains immersed in solvent 200 for a selected time or dwell time. Referring to FIG. 5C, mandrel 202 is then removed from solvent 200 as shown by an arrow 212. The cylindrical axis of mandrel 202 is perpendicular to the surface of the solution, although the mandrel can be removed at angle different from 90° to the solution surface. The use of a 90° angle is expected to facilitate uniformity in the coating thickness. Solution 210 is retained on mandrel 202 after removal from the solution 200 in container 204. Solvent is then removed from the retained solution 210 which results in the formation of a coating layer of the UHMW polymer. The solvent can be removed using various types of drying methods described below.

Other dip coating processes can be envisioned by those skilled in the art. These include immersing only a small part of the mandrel into the solution and while rotating parallel to the solution. This process helps ensure an even coating thickness.

In another embodiment, a hollow mandrel is dipped into the solution and a vacuum is drawn at one end of the mandrel causing the solution to be drawn into the mandrel. When the mandrel is lifted from the solution, the solution will drain from the inside leaving the inside to the mandrel coated with the polymer.

Figures 6A, 6B:
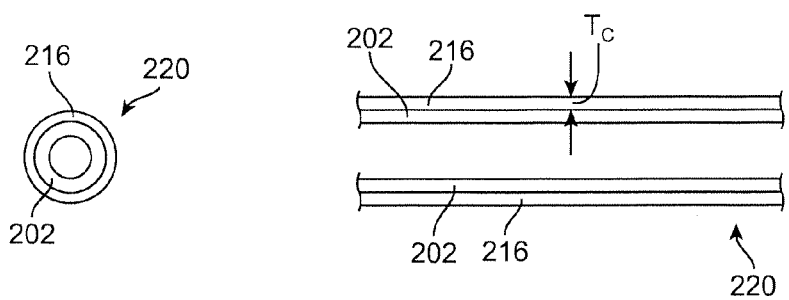
FIGS. 6A-B depict radial and axial cross-sections, respectively, of a coated mandrel.

If the coating layer is a desired thickness, the coating layer can be removed after solvent removal and machined to form stent. Alternatively, the steps in FIGS. 5A-C can be repeated one or more times until a desired thickness of polymer is achieved. In some embodiments, the coated tube can be rotated 180° before each coating step is repeated because gravity causes a greater volume of retained solution near a lower end of the mandrel after removal of the mandrel from the solution. FIGS. 6A-B depict radial and axial cross-sections, respectively, of a coated mandrel 220 that shows mandrel 202 with a polymer coating layer 216 with a thickness Tc.

There are several parameters in the dip coating process that can affect the quality and uniformity of the coating layer. It is desirable for the tubular coating layer to be uniform circumferentially and along the cylindrical axis. Parameters include the concentration and viscosity of the polymer solution, the dwell time in solution, and the rate of removal of the mandrel from solution.

In some embodiments, polymer concentration can be at or near a saturation concentration. Such concentration is expected to result in the highest viscosity and the thickest coating layer per immersion. Alternatively, polymer concentration can be less than saturation, for example, less than 50% or less than 25% saturation. A more dilute and less viscous solution may result in a coating layer. However, a more dilute solution will require a higher number of repeated coating steps to provide a final desired coating thickness.

The rate of removal of the mandrel from the solution can influence the uniformity of a coating layer of a single coating step and the consistency of thickness of coating layers deposited in separate steps. The inventor has found in the removal time ranges considered, the rate of removal is directly proportional to the uniformity of coating layer thickness along the cylindrical axis for a coating from a single step. As the rate decreases, there was a greater difference in coating thickness between the top end and bottom end of the mandrel. The inventor has also found that the removal rate is directly proportional to the consistency in thickness between coating layers deposited in separate steps.

A stent body or scaffolding with layers of different material, as shown (FIGS. 3A-B) and described above, can be formed from a tube having a wall with concentric layers of different material, with at least one layer being a UHMW polymer layer. Such a layer can be formed in several ways. In one method, both the UHMW polymer and the low molecular weight polymer layers can be formed by dip coating, as described above. For example, a UHMW layer of a desired thickness can be formed over a mandrel and then a low molecular weight polymer layer can be formed of a desired thickness over the UHMW polymer layer by dip coating or by spray coating. In another approach, a UHMW polymer layer may be formed by dip coating over a low molecular weight polymer tube formed from extrusion or injection molding. The low molecular weight polymer tube may or may not be disposed over a mandrel. When a mandrel is not used, this approach eliminates the step of removal of the dip coated tubular coating layer from a mandrel.

The solvent can be removed from the solution retained on the mandrel by methods known in the art including air drying or baking in an oven. In air drying a gas stream is directed on or blown onto the mandrel. The gas can be at room temperature or heated to increase the removal rate.

There are various ways to remove the tubular coating layer from the mandrel to further process the coating layer in the fabrication of a stent.

The coating layer can be formed over a mandrel made of a dissolvable material to be used as a dipping mandrel. After forming the coating layer, the mandrel can be dissolved by a solvent for the mandrel material, but that is a non-solvent for the coating polymer. In an exemplary embodiment, the mandrel is a wax and the coating polymer is PLLA.

In another method of removal, the tubular coating layer is formed over a hollow mandrel or pipe with one end of the pipe covered by the coating layer. The polymer is formed such that it wraps around the ends of the pipe, creating a seal. After completing the coating layer, the coating layer can be cut off one end of the polymer wrapped pipe. Compressed air blow into the open end forces the tube off the mandrel.

In another method, the coating layer is laser machined to form the stent pattern while still mounted on the mandrel.

Another method includes forming the coating layer over an inflated tubular balloon. The inflated tubular balloon is dip-coated as described above. Create a small scale balloon that is 3.2 mm inflated OD and dip-coat the balloon directly. After dip-coating, the balloon is deflated and removed from the coating layer.

In another removal method, the mandrel is heated after forming the coating layer. The heating is expected to loosen the coating layer, allowing it to be slipped off.

Another removal method includes application of oily or greasy coating over the mandrel before dip coating. Once dip coating is completed, the coating layer is slipped off.

In another method, a flexible rubber sleeve is wrapped around the mandrel prior to dip coating. After coating is complete, the tube may be pulled off the mandrel by the sleeve. The tube is then removed from the sleeve.

In another method, after dip coating over a metal mandrel, the metal mandrel is cooled sufficiently to cause shrinkage of the mandrel, allowing the coating layer to be pulled off.

In another method, a mechanical slider may be used to force the tube off of the mandrel.

An automated dip coating system can include a syringe pump that performs a controlled immersion into a polymer solution, dwell time in the polymer solution, and removal from the polymer solution of one or more mandrels. A syringe pump is a device designed to advance the plunger of a syringe at a consistent, precise rate for continuously controlled liquid delivery. A specially adapted mounting system for mandrels can be coupled to the plunger. The motion of the plunger is designed to provide controlled motion that immerses the mandrels at a controlled rate, to allow the mandrels to dwell in the solution for a selected time, and to provide controlled motion that removes the mandrels from the solution at a controlled rate. An exemplary syringe pump for automated dip coating is a Harvard Apparatus PHD 2000 programmable syringe pump.

FIG. 7 depicts a mandrel mounting disk 300 having a plurality of holes configured to hold mandrels for a dip coating operation. A plurality of mandrels 304 are mounted on mounting disk 300 within the holes. FIG. 8A depicts a system 310 for controlled dip coating of mandrels 304 mounted on mounting disk 300. System 310 has a syringe pump 320 positioned vertically and supported by a bracket 322. Syringe pump 320 includes a syringe plunger 324 that is coupled to mounting disk 300 on which are mounted a plurality of mandrels 304 (as illustrated in FIG. 7). In FIG. 8A, mounting disk 300 is positioned such that mandrels are immersed in a solvent within a container 328. Plunger 324 is configured to move downward, as shown by an arrow 330, at a controlled rate to immerse the mandrels in the solvent and then allow the mandrels to dwell in the solvent for a selected amount of time. FIG. 8B shows mounting disk 300 and mounted mandrels 304 removed from the solution. Plunger 324 is configured to move upward, as shown by an arrow 332, at a controlled rate to remove the mandrels from the solvent and is further configured to allow the mandrels to remain removed for a period of time to allow for removal of solvent from the solution retained on the mandrels.

One advantage of using the UHMW for a stent body is that a stent body machined from the tube as-formed has sufficient mechanical properties to support a bodily lumen without a radial expansion step to improve properties such as radial strength, modulus, and fracture toughness. In some embodiments, the radial expansion step could be eliminated as adequate mechanical properties can be achieved without the improvement that can be achieved as a result of radial expansion. in further embodiments, a UHMW polymer tube formed by methods described above can be radial expanded prior to laser machining to form a stent. In these embodiments, the stent can be formed from the expanded tube. The radial expansion tends to increase the radial strength and toughness of the polymer. The increase in strength is believed to be due the circumferential polymer chain orientation and an increase in crystallinity, both induced by the expansion. The radial expansion can be accomplished by a blow molding process. In such a process, the polymer tube is disposed within a cylindrical mold with a diameter greater than the polymer tube. The polymer tube is heated, preferably so that its temperature is above its Tg. The pressure inside of the tube is increased to cause radial expansion of the tube so the outside surface of the tube conforms to the inside surface of the mold. The polymer tube is than cooled below Tg and further processing steps can then be performed, such as laser machining.

The degree of radial expansion or deformation may be quantified by percent radial expansion:

$$\left[\frac{\text{Outside Diameter of Deformed Tube}}{\text{Original outside Diameter of Tube}} - 1\right] \times 100\%$$

In some embodiments, percent radial expansion can be 200-500%. In an exemplary embodiment, the percent radial expansion is about 300%. Similarly, the degree of axial deformation may be quantified by the percent axial elongation:

$$\left[\frac{\text{Length of Deformed Tube}}{\text{Original Length of Tube}} - 1\right] \times 100\%$$

In some embodiments, the tube can be elongated before during or after the radial expansion. The percent axial elongation can be 30-200%.

For the purposes of the present invention, the following terms and definitions apply:

"Compression molding" is a method of molding in which the molding material, generally preheated, is first placed in an open, heated mold cavity. The mold is closed with a top force or plug member, pressure is applied to force the material into contact with all mold areas, and heat and pressure are maintained until the molding material has cured. The process employs thermosetting resins in a partially cured stage, either in the form of granules, putty-like masses, or preforms.

"Ram extrusion" refers to a process in which a resin is fed from a hopper and packed into a cylinder in repeated increments by a reciprocating plunger. The frequency and amplitude of the plunger stroke can be controlled by an oil hydraulic system. The compressed material moves through a heated zone where it is fused into a profile matching the cross section of the barrel or die. The output rate is proportional to the length and frequency of the ram strokes. Die length, electrical heater capacity, hydraulic system power and maximum force, and the strength of the construction materials determine equipment capability.

"Molecular weight" can refer to the molecular weight of individual segments, blocks, or polymer chains. "Molecular weight" can also refer to weight average molecular weight or number average molecular weight of types of segments, blocks, or polymer chains.

The number average molecular weight (Mn) is the common, mean, average of the molecular weights of the individual segments, blocks, or polymer chains. It is determined by measuring the molecular weight of N polymer molecules, summing the weights, and dividing by N:

$$\overline{M}_n = \frac{\sum_i N_i M_i}{\sum_i N_i}$$

where Ni is the number of polymer molecules with molecular weight Mi. The weight average molecular weight is given by $$\overline{M}_w = \frac{\sum_i N_i M_i^2}{\sum_i N_i M_i}$$

where Ni is the number of molecules of molecular weight Mi.

The "inherent viscosity" (of a polymer) is the ratio of the natural logarithm of the relative viscosity, ηr, to the mass concentration of the polymer, c, i.e. ηinh=(ln ηr)/c, where the relative viscosity (ηr) is the ratio of the viscosity of a polymer solution, η, to the viscosity of the solvent (ηs), ηr=η/ηs.

"Ambient temperature" can be any temperature including and between 20° C. and 30° C.

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semicrystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. Tg of a given polymer can be dependent on the heating rate and can be influenced by the thermal history of the polymer. Furthermore, the chemical structure of the polymer heavily influences the glass transition by affecting mobility.

"Toughness" is the amount of energy absorbed prior to fracture, or equivalently, the amount of work required to fracture a material. One measure of toughness is the area under a stress-strain curve from zero strain to the strain at fracture. The units of toughness in this case are in energy per unit volume of material. See, e.g., L. H. Van Vlack, "Elements of Materials Science and Engineering," pp. 270-271, Addison-Wesley (Reading, Pa., 1989).

The underlying structure or substrate of an implantable medical device, such as a stent can be completely or at least in part made from a biodegradable polymer or combination of biodegradable polymers, a biostable polymer or combination of biostable polymers, or a combination of biodegradable and biostable polymers. Additionally, a polymer-based coating for a surface of a device can be a biodegradable polymer or combination of biodegradable polymers, a biostable polymer or combination of biostable polymers, or a combination of biodegradable and biostable polymers.

It is understood that after the process of degradation, erosion, absorption, and/or resorption has been completed, no part of the stent will remain or in the case of coating applications on a biostable scaffolding, no polymer will remain on the device. In some embodiments, very negligible traces or residue may be left behind. For stents made from a biodegradable polymer, the stent is intended to remain in the body for a duration of time until its intended function of, for example, maintaining vascular patency and/or drug delivery is accomplished.

Representative examples of polymers that may be used to fabricate an implantable medical device include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Another type of polymer based on poly(lactic acid) that can be used includes graft copolymers, and block copolymers, such as AB block-copolymers ("diblock-copolymers") or ABA block-copolymers ("triblock-copolymers"), or mixtures thereof.

Additional representative examples of polymers that may be especially well suited for use in fabricating or coating an implantable medical device include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol.

EXAMPLES

Some embodiments of the present invention are illustrated by the following examples. The examples are being given by way of illustration only and not by way of limitation. The parameters and data are not be construed to unduly limit the scope of the embodiments of the invention.

Example 1

Exemplary UHMW Resin for Use in Making Stent

A UHMW polylactide resin with brand name PURASORB PL and batch no. 0404002128 was obtained from PURAC located in the Netherlands. The properties of the resin are:

| | |
|---|---|
| Appearance: | white to light tan granules |
| Inherent Viscosity: | 8.36 dl/g (chloroform, 25° C., c = 0.1 g/dl) |
| Specific rotation (chloroform 25° C.) | −157.8 |
| Melting range (DSC, 10° C./mon) | 177.6-192.3° C. |
| Heat of fusion (DSC, 10° C./mon) | 74.1 J/g |
| Residual Solvent | <0.01% |
| Residual monomer | <0.1% |

Example 2

Illustration of Dip Coating Method with PLLA, Mw=2,200,000 g/Mole

PLLA tubes were made by dip coating with a solution of PLLA dissolved in chloroform. The concentration of the solution was a 2.5% weight by volume sample which provided uniform, complete dissolution.

80 mL of solution was prepared by dissolving PLLA using 78 mL of chloroform (Acros Organics: Chloroform, Extra Dry, Water <50 ppm, Fischer Science Catalogue number AC32682-0010) and 2.5 g of PLLA granules received from PURAC biochem, Gorinchem, The Netherlands. The solution was dissolved overnight in a closed container within a fume hood.

Once the solution was prepared, a dipping apparatus was set up with a metal mandrel of 0.125 in diameter. Mandrels were lowered by hand into the solution and removed manually at an approximate rate of 1, 2, or 3 cm per second. The solvent was then allowed to evaporate.

Coating thickness was determined by caliper measurement after each coat per the following formula: Tw=(Ti−Tm)/2, where Tw is the wall thickness, Ti is the total thickness (measured) and Tm is the fixed mandrel thickness (0.125 in). This process was continued until appropriate wall thickness was obtained, 0.006 in. Tubes were made using three different removal times from the solution: 15 seconds, 30 seconds, and 45 seconds.

Figure 9:
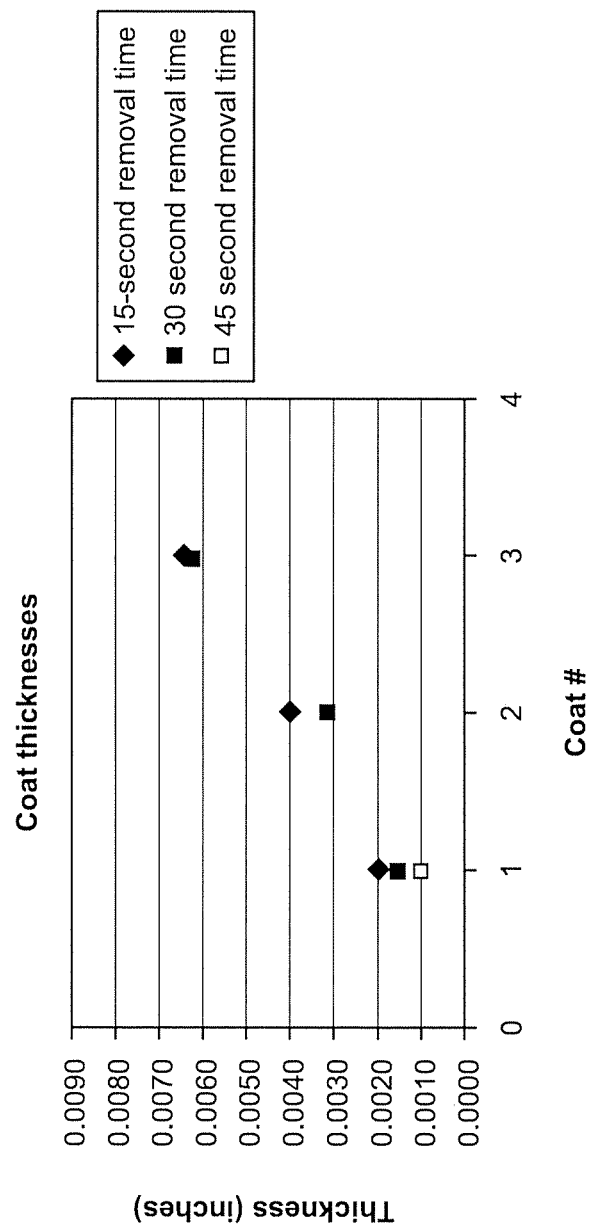
FIG. 9 depicts the results of a dip coating operation.

The results from the dip coating are shown in FIG. 9. The average coating thickness of each of the three coats is shown. A longer removal time corresponds to a slower speed of mandrel removal. As shown in FIG. 9, the runs of fastest removal time resulted in the most linear relationship of thickness along the length of the tube. A slower velocity of mandrel removal from the solution resulted in a greater difference in thickness at the bottom of the tube compared to other sections. This could be due to the greater amount of time allowed to the polymer solution to flow down the length of the tube due to the pull of gravity.

Example 3

Exemplary Dip Coating Process

1. Mix 195 ml chloroform and 6.25 g polymer to create 200 ml of solution (2.5 wt %) need to mix solution until all granules have dissolved (using stir bar with stir plate at 250 rpm)
2. Fill up dip container with solution to the marked line
3. Place hollow mandrels (0.125") into fixture
4. Dip mandrels for 30 seconds, let dry for 30 minutes
5. Invert mandrel and repeat 3 more times (total 4 dips, invert mandrels after every dip)
6. Put tubes into vacuum at room temperature for 48 hours
7. Cut the tubes to 110 mm and remove the tubes from the mandrels using the mechanical slider and place the tubes on the solid mandrels (0.123")
8. Put tubes back into vacuum for 24 hours
9. Cut tubes to 100 mm in length
10. After 24 hours, measure the proximal, middle, and distal ID and OD
11. Remove tubes from mandrels While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of making a stent body for supporting a vascular lumen, comprising:
   immersing a cylindrical member in a solution including a bioabsorbable polymer dissolved in a fluid, wherein the bioabsorbable polymer has an inherent viscosity greater than 6 dl/g or has a weight average molecular weight greater than 1 million g/mole, wherein the bioabsorbable polymer is poly(L-lactide) (PLLA);
   removing the member from the solution, wherein a portion of the solution remains on the surface of the member upon removal from the solution;
   removing solvent from the solution remaining on the member to form a tubular layer of the bioabsorbable polymer on the member;
   repeating the immersion step, removal from the solution step, and removal of the solvent step to form a final tubular layer of bioabsorbable polymer on the member of a desired thickness; and
   forming a stent body from the final tubular layer, wherein the final tubular layer consists essentially of PLLA, wherein a degree of crystallinity of the final tubular layer is less than 25%.

2. The method of claim 1, wherein a degree of crystallinity of the final tubular layer is 15-25%.

* * * * *